United States Patent [19]

Mohrmann et al.

[11] Patent Number: 4,898,954

[45] Date of Patent: Feb. 6, 1990

[54] PROCESS FOR THE PREPARATION OF OXIRANES

[75] Inventors: Karl H. Mohrmann; Wolf Reiser, both of Wuppertal, Fed. Rep. of Germany; Siegfried W. Linke, Seoul, Rep. of Korea; Rudolf Zerbes, Wuppertal, Fed. Rep. of Germany

[73] Assignee: Bayer Aktiengesellschaft, Leverkusen, Fed. Rep. of Germany

[21] Appl. No.: 772,066

[22] Filed: Sep. 3, 1985

Related U.S. Application Data

[63] Continuation of Ser. No. 603,527, Apr. 25, 1984, abandoned.

[30] Foreign Application Priority Data

Apr. 29, 1983 [DE] Fed. Rep. of Germany ....... 3315681

[51] Int. Cl.[4] ............................................ C07D 301/02
[52] U.S. Cl. .................................................... 549/519
[58] Field of Search .......................................... 549/519

[56] References Cited

U.S. PATENT DOCUMENTS

| | | | |
|---|---|---|---|
| 4,162,258 | 7/1979 | Higo et al. | 549/332 |
| 4,230,719 | 10/1980 | Kodama et al. | 549/79 |

FOREIGN PATENT DOCUMENTS 40345  11/1981  European Pat. Off.

OTHER PUBLICATIONS

V. Franzen et al., Berichte, vol. 96, (163), pp. 1881–1890.
E. J. Corey et al., J.A.C.S., vol. 87(6), (1965), pp. 1353–1364.
E. J. Corey et al., J.A.C.S., vol. 84, (1962), pp. 3782–3.
C. R. johnson et al., J.A.C.S., vol. 95(22), (1973), pp. 7424–7431.
T. Kutsuma et al., Heterocycles, vol. 8, (1977), pp. 397–401.
Fieser & Fieser, Reagents for Organic Synthesis, vol. 5, (1975), pp. 549–550.
Fieser & Fieser, Reagents for Organic Synthesis, vol. 1, (1967), pp. 911–914.

*Primary Examiner*—Glennon H. Hollrah
*Assistant Examiner*—Mark W. Russell
*Attorney, Agent, or Firm*—Sprung Horn Kramer & Woods

[57] ABSTRACT

A process for the preparation of oxiranes is disclosed in which trimethylsulphonium methyl sulphate, formed by treating dimethyl sulphide with dimethyl sulphate in the presence of tert.-butanol, is reacted, without previous isolation, with a ketone in the presence of a base and in the presence of tert.-butanol. The resultant oxiranes are useful in the preparation of plant growth regulants and fungicides.

8 Claims, No Drawings

PROCESS FOR THE PREPARATION OF OXIRANES

This a continuation of application Ser. No. 603,527, filed April 25, 1984 now abandoned.

The present invention relates to a new process for the preparation of known oxiranes which can be used as intermediates for the synthesis of compounds having plant-growth regulating and fungicidal activity.

It has already been disclosed that oxiranes can be prepared by reacting dimethyl sulphide and dimethyl sulphate and then reacting the trimethylsulphonium methyl sulphate, which is formed thereby as an intermediate, with carbonyl compounds in the presence of an inert organic solvent and in the presence of a strong base, such as acetonitrile (compare J. Amer. Chem. Soc. 87, 1353–1364 (1965) and Ber. 96, 1881–1890 (1963)).

It has also been disclosed that 2-(4-chlorophenylethyl)-2-tert.-butyloxirane can be prepared by reacting the trimethylsulphonium methyl sulphate, which is prepared from dimethyl sulphide and dimethyl sulphate, with 1-(4-chlorophenyl)-4,4-dimethyl-3-pentanone in acetonitrile in the presence of sodium methylate (compare EP-OS (European Published Specification) 40,345). The yields in this process are good but, nevertheless, are not always adequate for practical purposes. Moreover, relatively long reaction times are necessary for the process.

It has now been found that the known oxiranes of the formula

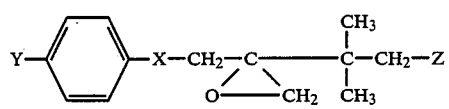

in which
Y represents chlorine or phenyl,
X represents oxygen or $CH_2$ and
Z represents hydrogen or halogen,
are obtained when dimethyl sulphide is treated with dimethyl sulphate in the presence of tert.-butanol, and the trimethylsulphonium methyl sulphate produced thereby, of the formula $$(CH_3)_3S^\oplus \ CH_3SO_4^\ominus \qquad (II)$$

is reacted, without previous isolation, with a ketone of the formula

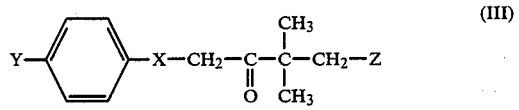

in which
X, Y and Z have the meanings indicated above, in the presence of a base and in the presence of a tert.-butanol, at temperatures between 0° and 60° C.

It has to be denoted extremely surprising that oxiranes of the formula (I), for example 2-(4-chlorophenylethyl-2-tert.-butyloxirane can be prepared by the process according to the invention in higher yields than in the hitherto known processes in which acetonitrile was used as the solvent. It is also surprising that specifically tert.-butanol is particularly well suited as the solvent, while the reaction does not provide the desired result in the presence of other low boiling alcohols.

The process according to the invention has a number of advantages. Thus, it makes it possible to prepare oxiranes of the formula (I) in very good yields. Moreover, the starting materials are relatively reasonably priced and available on an industrial scale. Furthermore, the reaction times are considerably shorter than for the hitherto known processes for the preparation of the oxiranes of the formula (I).

The oxiranes which can be prepared by the process according to the invention are defined by the formula (I). In this formula, X represents oxygen or the $CH_2$ group and Y represents chlorine or phenyl. The radical Z preferably represents hydrogen, fluorine or chlorine.

When, in addition to dimethyl sulphide and dimethyl sulphate, 1-(4-chlorophenyl)-4,4-dimethyl-3-pentanone is used as the starting material and sodium methylate is used as the base in the process according to the invention, the the course of the reaction can be illustrated by the diagram below:

$$(CH_3)_2S + (CH_3)_2SO_4 \longrightarrow (CH_3)_3S^\oplus \ CH_3SO_4^\ominus \qquad (a)$$

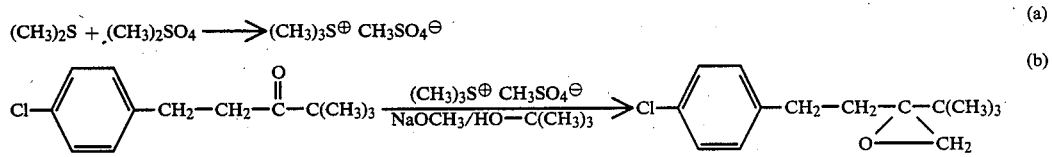

(b)

The ketones necessary as starting materials for the process according to the invention are defined by the formula (III). In this formula, Y represents chlorine or phenyl and X represents oxygen or the $CH_2$ group. The radical Z preferably represents hydrogen, fluorine or chlorine.

The ketones of the formula (III) are known (compare German Patent Specification 2,201,063, DE-OS (German Published Specification) 2,705,678 and DE-OS (German Published Specification) 2,737,489).

The trimethylsulphonium methyl sulphate of the formula (II) which is also necessary as a starting material for the process according to the invention is likewise known (compare Heterocycles 8, 397 (1977)). It is employed in the above reaction in the freshly prepared state by producing it by reaction of dimethyl sulphide with dimethyl sulphate and using it further without previous isolation.

Strong inorganic and organic bases can be used as bases for the process according to the invention. Suitable and preferred are sodium hydride, sodium amide, also alkali metal alcoholates, such as sodium methylate, sodium ethylate and potassium tert.-butylate, moreover potassium hydroxide.

In carrying out the process according to the invention, the reaction temperatures can be varied within a certain range. In general, both for the preparation of the trimethylsulphonium methyl sulphate and for its subsequent reaction with a ketone of the formula (III), the temperatures are between 0° and 60° C., preferably between 10° and 50° C.

The process according to the invention is generally carried out under normal pressure. However, it is also possible to carry it out under elevated or reduced pressure.

In carrying out the process according to the invention, the amounts of the components in the reaction are generally selected such that 1.0 to 2.2 mole, preferably 1.0 to 1.5 mole, of dimethyl sulphide, 1.0 to 2.0 mole, preferably 1.0 to 1.5 mole, of dimethyl sulphate and 1.0 to 4.0 mole, preferably 1.0 to 2.0 mole, of base are generally employed for 1 mole of ketone of the formula (III).

The specific procedure for carrying out the process according to the invention is such that dimethyl sulphide and dimethyl sulphate are fixed in tert.-butanol, this solution is stirred for several hours and added to a mixture of ketone of the formula (III) and base in tert.-butanol. Working up is by customary methods. In general, the procedure is such that an oxidising agent, such as, for example, aqueous hydrogen peroxide solution or a mixture of dilute aqueous sodium hypochlorite or potassium hypochlorite solution and an organic solvent which is poorly miscible with water and water are added to the reaction mixture, and the organic phase is then separated off, washed and evaporated after previous drying if necessary. The product resulting thereby can be distilled under reduced pressure for further purification.

The oxiranes of the formula (I) which can be prepared by the process according to the invention are valuable starting materials for the synthesis of 1-hydroxyethylazole derivatives which have outstanding plant-growth regulating and fungicidal properties (EP-OS (European Published Specification) 40,345).

Thus, for example, 1-(4-chlorophenyl)-4,4-dimethyl-3-(1,2,4-triazol-1-ylmethyl)-3-pentanol of the formula

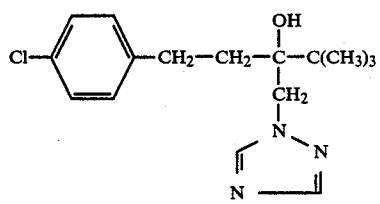

can be prepared by reacting 2-(4-chlorophenylethyl)-2-tert.-butyloxirane with 1,2,4-triazole in the presence of potassium hydroxide. This synthesis can be illustrated by the formulae below:

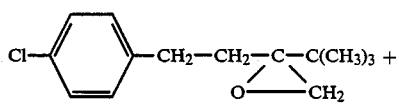

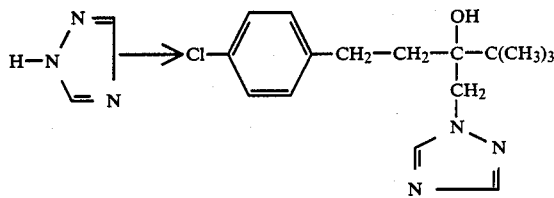

The process according to the invention is illustrated by the examples which follow.

EXAMPLE 1

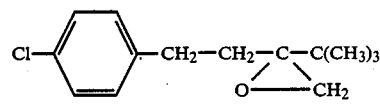

94.5 g (0.75 mole) of dimethyl sulphate were slowly added dropwise, with stirring, at room temperature to a mixture of 53 g (0.85 mole) of dimethyl sulphide in 150 ml of tert.-butanol, during which the temperature of the reaction mixture rose to 65° C. The mixture was stirred for 4 hours and then, while cooling in an ice bath, 117 g (0.5 mole) of a product which consisted of 96% of 1-(4-chlorophenyl)-4,4-dimethyl-3-pentanone were added. Then 112.2 g (1 mole) of potassium tert.-butylate were rapidly added, during which the temperature of the reaction mixture rose to 40° C. Then the volatile constituents were distilled out up to a top temperature of 82° C. 2 liters of water and 200 ml of an aqueous sodium hypochlorite solution were consecutively added to the remaining residue. Then 500 ml of toluene were added and the phases were separated. The organic phase was washed with water to neutrality, filtered and concentrated under reduced pressure. An oily residue weighing 113 g which, according to the gas chromatogram, consisted of 93% of 2-(4-chlorophenylethyl)-2-tert.-butyloxirane remained. A yield of 88.1% of theory was calculated from this.

COMPARISON EXAMPLE

Preparation of 2-(4-chlorophenylethyl)-2-tert.-butyloxirane of the formula

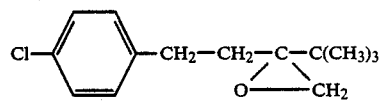

by a known process.

A solution of 108 ml (1.47 mole) of dimethyl sulphide in 130 ml of acetonitrile was added dropwise, with stirring, to a solution of 126 ml (1.33 mole) of dimethyl sulphate in 670 ml of acetonitrile. The reaction mixture was allowed to stand overnight and then 79.2 g (1.47 mole) of solid powdered sodium methylate were added, the temperature of the reaction mixture being maintained at about 20° C. Then a solution of 179 g (0.8 mole) of 1-(4-chlorophenyl)-4,-dimethyl-3-pentanone in 250 ml of acetonitrile was added dropwise. The reaction mixture was stirred for 4 hours and then allowed to stand overnight. The reaction mixture was then concentrated under reduced pressure, and the remaining residue was dissolved in ethyl acetate. The solution produced thereby was washed with water and, after drying over sodium sulphate, was concentrated by removing the solvent under reduced pressure. The residue remaining was subjected to vacuum distillation. 157 g of a product which had a boiling point of 102°–105° C. at 0.01 mbar and which, according to the gas chromatogram, consisted of 53% of 2-(4-chlorophenylethyl)-2-tert.butyloxirane were obtained in this manner. A yield of 43% of theory was calculated from this.

EXAMPLE FOR THE USE OF AN OXIRANE WHICH CAN BE PREPARED ACCORDING TO THE INVENTION FOR THE SYNTHESIS OF A 1-HYDROXYETHYLAZOLE DERIVATIVE HAVING PLANT-GROWTH REGULATING AND FUNGICIDAL ACTIVITY

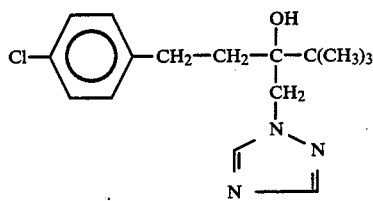

A solution of 27.1 g (0.1 mole) of a product which consisted of 88% of 2-(4-chlorophenylethyl)-2-tert.-butyloxirane, 8.3 g (0.12 mole) of 1,2,4-triazole and 0.06 g (0.01 mole) of potassium hydroxide in 100 ml of n-propanol was heated at 95° C. for 30 hours. It was then allowed to cool and the reaction mixture was concentrated by removing the solvent under reduced pressure. The residue remaining was taken up in toluene, the suspension produced thereby was filtered and the filtrate was concentrated by removing the solvent under reduced pressure. The resulting residue was recrystallised from ligroin. 30.6 g of a product which, according to HPLC analysis, consisted of 67.4% of 1-(4-chlorophenyl)-4,4-dimethyl-3-(1,2,4-triazole-1-ylmethyl)-3-pentanol were obtained in this manner. A yield of 67% of theory was calculated from this.

What is claimed is:

1. A process for the preparation of an oxirane of the formula

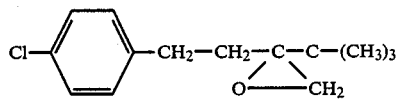

which comprises contacting dimethyl sulphide with dimethyl sulphate in the presence of tert.-butanol thereby to form trimethylsulphonium methyl sulphate of the formula

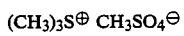

and thereafter, without isolating said trimethylsulphonium methyl sulphate, contacting the same with 1-(4-chlorophenyl)-4,4-dimethyl-3-pentanone in the presence of potassium tert.-butylate and in the presence of tert.-butanol at temperatures between 0° and 60° C.

2. A process according to claim 1, wherein the process is carried out under normal pressure.

3. A process according to claim 1, wherein the process is carried out under elevated pressure.

4. A process according to claim 1, wherein the process is carried out under reduced pressure.

5. A process according to claim 1, wherein 1.0 to 2.2 moles of dimethyl sulfide, 1.0 to 2.0 moles of dimethyl sulfate and 1.0 to 4.0 moles of potassium tert.-butylate are employed per mole of 1-(4-chlorophenyl)-4,4-dimethyl-3-pentanone.

6. A process according to claim 1, wherein 1.0 to 1.5 moles of dimethyl sulfide, 1.0 to 1.5 moles of dimethyl sulphate and 1.0 to 2.0 moles of potassium tert.-butylate are employed per mole of 1-(4-chlorophenyl)-4,4-dimethyl-3-pentanone.

7. A process according to claim 6, wherein the pentanone is first added to the solution of the trimethylsulphonium methyl sulphate and then the potassium tert.-butylate is added.

8. A process according to claim 1 wherein the process is carried out under a temperature between 10° and 50° C.

* * * * *